US00PP27440P3

(12) United States Plant Patent
Roe

(10) Patent No.: US PP27,440 P3
(45) Date of Patent: Dec. 6, 2016

(54) TANGERINE TREE NAMED 'WG32'

(50) Latin Name: *Citrus reticulata*
Varietal Denomination: WG32

(71) Applicant: Bill Roe, Eagle Lake, FL (US)

(72) Inventor: Bill Roe, Eagle Lake, FL (US)

(73) Assignee: GJH LLC, Winter Haven, FL (US)

( * ) Notice: Subject to any disclaimer, the term of this patent is extended or adjusted under 35 U.S.C. 154(b) by 93 days.

(21) Appl. No.: 14/121,774

(22) Filed: Oct. 15, 2014

(65) Prior Publication Data

US 2016/0113172 P1 Apr. 21, 2016

(51) Int. Cl.
*A01H 5/08* (2006.01)

(52) U.S. Cl.
USPC ..... Plt./201

(58) Field of Classification Search
USPC ..... Plt./201, 202
See application file for complete search history.

(56) References Cited

U.S. PATENT DOCUMENTS

PP25,151 P3 * 12/2014 Grosser ..... A01H 5/0806 Plt./201
2015/0237783 P1 * 8/2015 Grosser ..... A01H 5/0806 Plt./201

* cited by examiner

*Primary Examiner* — June Hwu
(74) *Attorney, Agent, or Firm* — Cassandra Bright

(57) ABSTRACT

A new and distinct *Citrus reticulata* cultivar named 'WG32' is disclosed, characterized by having distinctive oblate shaped fruit with a distinctive stem end nipple. Trees fruit heavily, producing both large and below average sized fruit, with different peeling characteristics. The new cultivar is a *Citrus reticulata*, useful for commercial fruit production.

4 Drawing Sheets

Latin name of the genus and species: *Citrus reticulata.*
Title: Tangerine Tree Named 'WG32'.

BACKGROUND OF THE INVENTION

The new cultivar is a product of a planned breeding program conducted during 2000 under the direction of the inventor, Bill Roe, a citizen of The United States. The seed parent is the unpatented commercial variety *Citrus reticulata* 'Lee', the pollen parent is an unnamed, unpatented proprietary *Citrus reticulata.*

This new variety was found in November 2006 in a commercial nursery in Winter Haven, Fla. Plants were first propagated by tissue culture, using embryo culture, in 2006 and subsequently grafted onto rootstocks US-897 and US-942. Development, evaluation, tissue culture and grafting all first took place at the inventor's commercial nursery in Winter Haven, Fla. USA. Subsequent evaluations of the variety have shown the characteristics to be true to type.

SUMMARY OF THE INVENTION

The cultivar 'WG32' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WG32'. These characteristics in combination distinguish 'WG32' as a new and distinct *Citrus reticulata* cultivar:

1. Fruit develops unique stem end nipple.
2. Trees fruits heavily with below average size fruit.

3. Has distinct high note flavor profile (both acid and brix).
4. Ripens during Late October and November window; fruit less than moderately firm. Fruit is tender to the touch and can easily bruise at 50% color break.
5. Two different peeling characteristics; larger fruit peels easier than smaller fruit.
6. Fruit colors up on the tree without degreening.
7. Average of 10-12 seeds per fruit.

COMPARISON TO PARENT VARIEITES

Plants of the new cultivar 'WG32' are similar to plants of the seed parent, *Citrus reticulata* 'Lee' in most horticultural characteristics, however, plants of the new cultivar 'WG32' differs in the following ways;

1. Stem end nipple is much more pronounced.
2. Smaller fruit size.
3. Fruit is more oblate.

Plants of the new cultivar 'WG32' are similar to plants of the pollen parent, in most horticultural characteristics, however, plants of the new cultivar 'WG32' differ in the following;

4. Stem end protrusion is more pronounced.
5. Smaller fruit size.
6. More uniform fruit color.
7. Higher acid content.
8. Peel adheres more tightly.
9. Does not appear to be susceptible to *Alternaria* fungal attacks.

COMMERCIAL COMPARISON

The new variety is best compared to the commercial variety, 'Dancy,' unpatented. 'WG32' is similar to 'Dancy' in many horticultural characteristics; however, 'WG32' differs in the following ways;

1. Has tighter peel.
2. Has a more consistently pronounced nipple.
3. Average fruit size is smaller.
4. Fruit on the tree is more uniform in color.
5. More compact tree size.
6. Less limb breakage.

'WG3' can also be compared to 'Sunburst', unpatented. The two varieties are similar in many horticultural characteristics; however 'WG32' differs in the following ways;

1. Rougher peel
2. More pronounced and distinct stem and nipple.
3. Easier to peel fruit, with less albedo.
4. Lower seed count.
5. Less deep orange in external color.

BRIEF DESCRIPTION OF THE PHOTOGRAPH

The accompanying photograph in FIG. 1 illustrates in full color examples of typical fruit harvested from 'WG32'.

Figure 1:
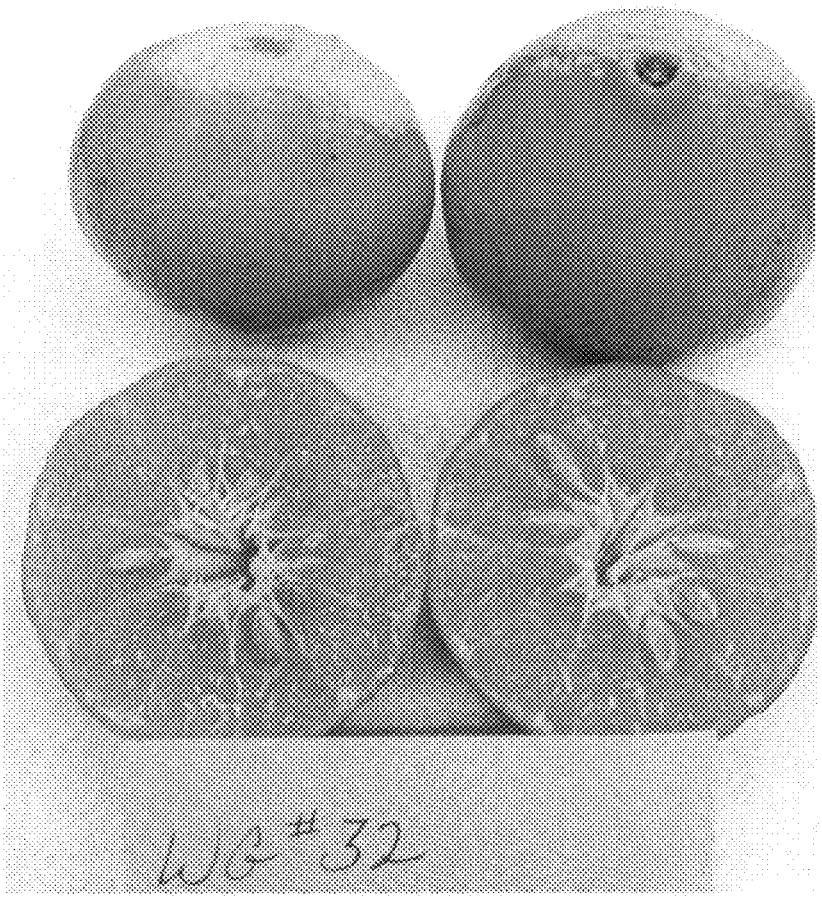
Figure 2:
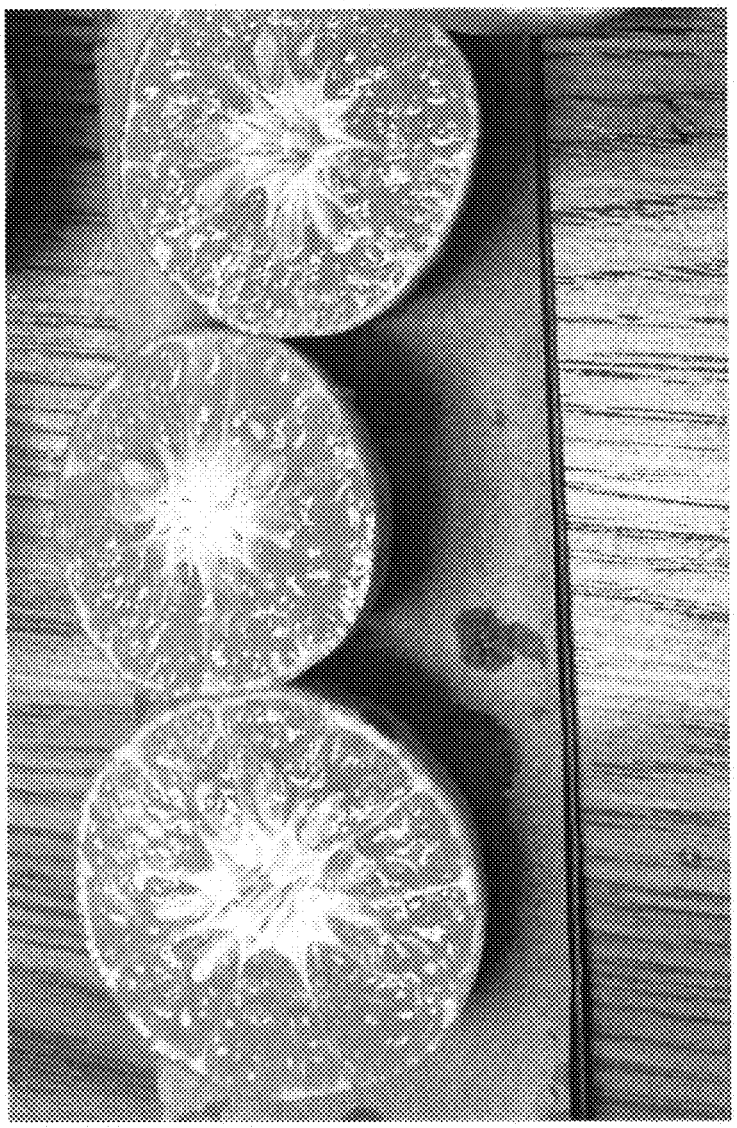
FIG. 2 illustrates in full color the interior of the fruit.
Figure 3:
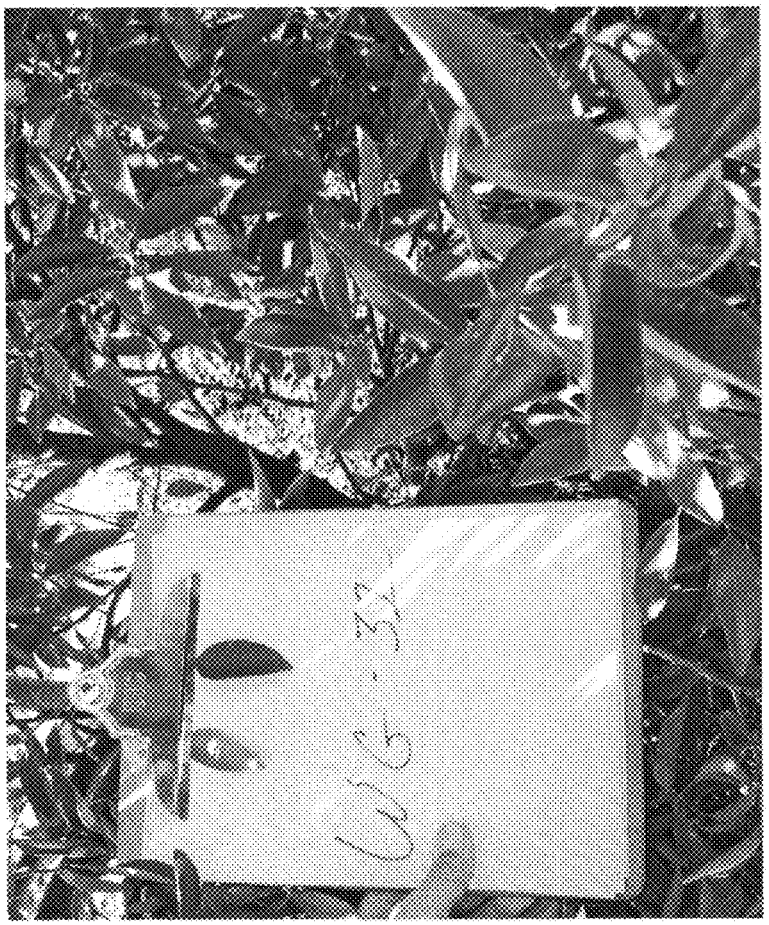
FIG. 3 illustrates branches and typical foliage of 'WG32'.
Figure 4:
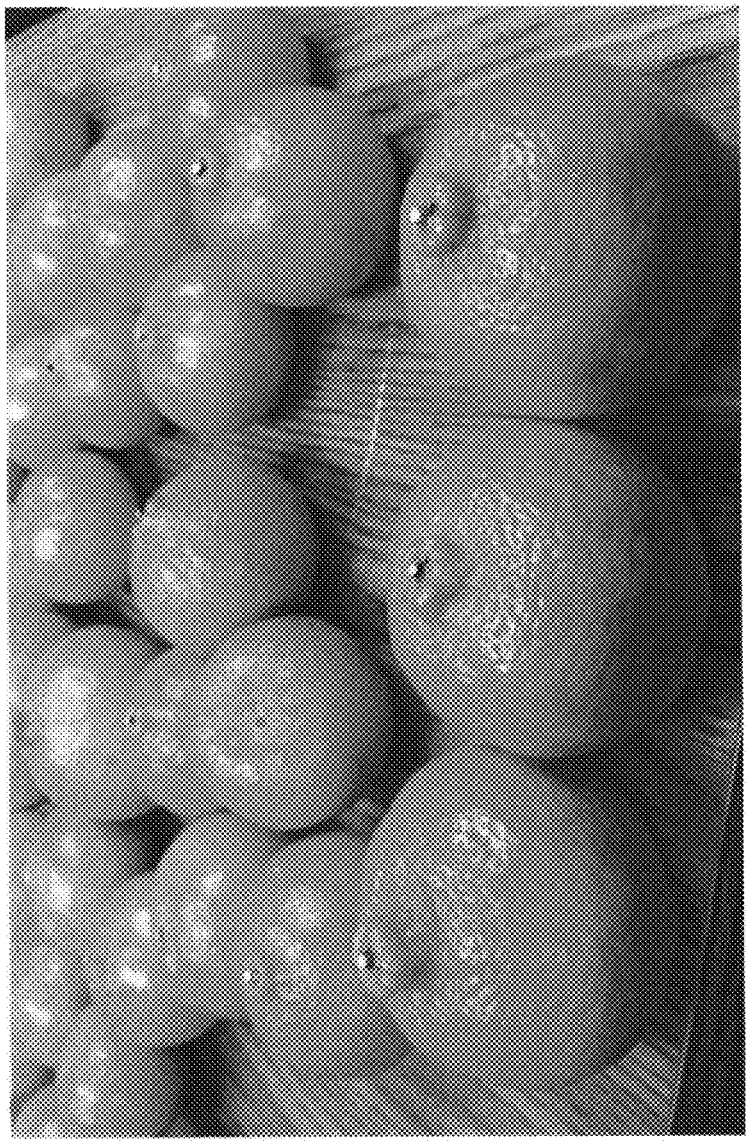
FIG. 4 illustrates the typical fruit shape of 'WG32'.

Photographs are taken of plants approximately 2 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'WG32' plants grown outdoors under commercial trial conditions in Winter Haven, Fla. USA. The growing temperature ranged from 10° C. to 35° C. during the day and −4° C. to 20° C. at night. Measurements and numerical values represent an average from the most typical specimens.

Botanical classification: *Citrus reticulata* 'WG32'.

PROPAGATION

'WG32' is typically grafted onto rootstock of *Citrus reticulata* US-897 and US-942

PLANT

Age of the plant described: Approximately 2 to 3 years.

Plant habit: Upright with weeping and flexible limbs, consistent growth habit—plants in a row are similar in size.

Height: Approximately 185 cm.

Growth rate: Approximately 3 years to 185 cm.

Plant spread: Approximately 180 cm, depending upon pruning.

Length of primary lateral branches: Approximately 52-72 cm.

Quantity of lateral branches: 2-4.

Angle of lateral branches from main trunk: 150-170° degrees.

Branching arrangement: Typically 2-3 more vertical main limbs with 1-2 smaller and more horizontal shoots. The vertical shoots rebranch after 52-72 cm.

Branch diameter: Average 3.8-5.0 cm.

Trunk texture: Minimally rough, slightly striated.

Trunk color: Near RHS Grey-Brown N199A.

Trunk diameter: Average 8.0 cm on a 3 year old plant.

Spines:

*Density*.—Minimal, less than moderate, nearly absent.

*Size*.—Average length about 1 cm. Base approximately 0.4 cm in diameter.

*Color*.—Near RHS Greyed-Green 197C.

FOLIAGE

Leaf:

*Average length*.—Range: 6.5-8.25 cm. Average of 7.6 cm.

*Average width*.—Range: 2.8 3.9 cm. Average of 3.2 cm.

*Shape of blade*.—Elliptic.

*Apex*.—Acute.

*Base*.—Broad attenuate.

*Attachment*.—Petioled.

*Margin*.—Very infrequent, shallow dentations.

*Texture of top surface*.—Smooth.

*Texture of under side*.—Smooth with raised center rib.

*Aspect*.—Foliage typically upwardly folded. No twisting or blistering with normal cultural conditions.

*Color*.—Mature foliage upper side: Near RHS Green 137A. Mature foliage under side: Near RHS Green 138A.

*Petiole*.—Length: Average length 0.75-1.6 cm. Width: Average 0.3 cm. Pubescence: None. Color: Upper and lower surfaces near Green 143B. Petiole Wing: Approximately 7 mm to 1.6 average length. Approximately 2 to 3 mm wide. Color and texture identical to leaf.

FLOWER

Inflorescence and flower type and habit: Single rotate flowers emerging from leaf axils.

Flowering period: Typical peak flowering occurs in Florida between March 15 and March 25.

Flower longevity on plant: Approximately 2 weeks.

Persistent or self-cleaning: Self-cleaning.

Bud:

*Shape*.—A small popcorn bud that elongates to a blunt nosed cylindrical bud.

*Length*.—Average 8-9 mm.

*Diameter*.—Average 5 mm.

*Color*.—Near RHS White 155A.

Flower size:

*Diameter*.—Average 2.2-2.3 cm.

*Depth*.—Average 1.0 cm.

Corolla/petals:

*Arrangement*.—Rotate, fused at base.

*Petal quantity*.—5.

*Length*.—Average 18-10 mm.

*Width*.—Average 2.5 to 3.0 mm.

*Texture*.—Smooth without pubescence.

*Apex*.—Acute.

*Base*.—Fused.

*Margin*.—Smooth.

Color: Petals are white upon abscission.

Calyx/sepals: Filaments separate easily.

*Quantity per flower*.—5.

*Shape*.—Straight.

*Length*.—Average 6-7 mm.

*Width*.—Average 1 mm.

*Texture*.—Smooth.

*Color*.—Upper Surface: Near RHS Green 137A. Lower Surface: Near RHS Green 137A.

Pedicel:

*Length*.—Average 4-5 mm.

*Diameter*.—Average 1 mm.

*Color*.—Near RHS Green 137A.

*Texture*.—Smooth without pubescence.

Fragrance: Sweet, typical *Citrus* flower scent.

REPRODUCTIVE ORGANS

Stamens:

*Number*.—Most commonly 12.

*Filament length*.—Approximately 2.2 cm.

Anthers:

*Shape*.—Globular.

*Length*.—Approximately 0.2 cm.

*Color*.—Near RHS Yellow-White 158A.

*Pollen*.—Color: Near RHS Yellow 8C. Quantity: Moderate.

Pistil:

*Number*.—1.

*Length*.—Approximately 0.8 cm.

*Style*.—Length: 0.6 cm. Color: Near RHS Green-Yellow 1D.

*Stigma*.—Shape: linear. Color: Near RHS Yellow 8D. Ovary Color: RHS Green 143C.

FRUIT

Color exocarp: Near RHS Orange N25A.

Color mesocarp: Near RHS Yellow-Orange 19C.

Flesh color: Near RHS Orange N25B.

Brix at consumption: 12.50.

Brix at harvest: 11.80. Acid 1.0 Ratio of 12.50.

Average weight: Fruit size varies, more accurately described by minimum and maximum weights.

Minimum weight: 100 grams.

Maximum weight: 246 grams.

Height: 5.8-6.4 cm. Average 6.2 cm.

Width: 7-7.7 cm. Average of 7.5.

Segment number per fruit: 9 to 11.

Segment size:

*Average width*.—1.5 cm.

*Average length*.—4.2 cm.

Fruit peduncle length: 1-2 cm.

Fruit peduncle width: 4 to 6 mm.

General shape: Oblate. Pronounced nipple protrusion at top.

*Proximal shape*.—Obtuse rounded, not quite flat.

*Distal shape*.—Flat to nearly rounded.

Neck length: 4 to 7 mm.

Neck width: 5 to 1.2 mm.

Neck constriction: Constriction typically present, typically pronounced to moderate.

Neck depression: Typically absent.

Skin/rind texture: Slightly bumpy with oil glands.

Oil glands: Mostly large, interspersed with small.

Rind adherence: Moderate to smaller fruit exhibit tight adherence to lower half of fruit, moderate adherence in upper half of fruit. Largest fruit exhibits loose skin adherence.

Rind oil: Moderate quantity of oil. Inner surface oil glands conspicuous.

Albedo: Colored near Yellow 10D. Less than average density to flesh. Minimal adherence to flesh, adhering only in strands. Moderate albedo strand presence.

Fruit core: Sparse.

Rudimentary segments: Absent.

Segment wall strength: Weak.

Fruit juiciness: High.

Harvest time: Late October.

Overall cropping quantity: Crops very heavily with a range of fruit sizes.

Mature seed color: Near RHS Greyed-Yellow 161D.

Quantity seed per fruit: Average 10 to 12.

Seed shape: Ovoid.

Seed length: 10-13 mm. Average of 12 mm.

Seed width: 5.5-7 mm.

OTHER CHARACTERISTICS

Storage life: Storage life is a minimum of 60 plus days at 2° C. Fruit does not dry out.

Disease/pest resistance: 'WG32' has been observed not to be susceptible to *Alterneria* fundal diseases. No other susceptibility nor resistance observed.

Temperature tolerance: Tolerates low temperatures to approximately −5° C. without negative effects, tolerates high temperatures to approximately 37° C. without negative effects.

What is claimed is:

1. A new and distinct Tangerine tree named 'WG32' as herein illustrated and described.

* * * * *